United States Patent
Wesselink et al.

(10) Patent No.: US 7,292,168 B2
(45) Date of Patent: Nov. 6, 2007

(54) DSP WITH VARIABLE SAMPLE FREQUENCY

(75) Inventors: Willem A. Wesselink, Doesburg (NL); Henricus W. M. De Bruyn, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/320,358

(22) Filed: Dec. 28, 2005

(65) Prior Publication Data

US 2007/0146189 A1 Jun. 28, 2007

(51) Int. Cl.
*H03M 1/00* (2006.01)

(52) U.S. Cl. .................. 341/123; 607/16; 607/57; 607/509; 607/5

(58) Field of Classification Search ........... 341/123; 607/5, 17, 16, 509
See application file for complete search history.

(56) References Cited

U.S. PATENT DOCUMENTS

| | | | |
|---|---|---|---|
| 4,532,930 A * | 8/1985 | Crosby et al. ............ 607/57 |
| 5,158,078 A | 10/1992 | Bennett et al. | |
| 5,224,475 A | 7/1993 | Berg et al. | |
| 5,226,513 A | 7/1993 | Shibayama | |
| 5,314,448 A | 5/1994 | Kroll et al. | |
| 5,318,593 A | 6/1994 | Duggan | |
| 5,366,485 A | 11/1994 | Kroll et al. | |
| 5,564,434 A | 10/1996 | Halperin et al. | |
| 5,713,924 A | 2/1998 | Min et al. | |
| 5,835,975 A | 11/1998 | Peeters et al. | |
| 6,236,888 B1 * | 5/2001 | Thompson ............... 607/16 |
| 6,512,944 B1 * | 1/2003 | Kovtun et al. ........... 600/509 |
| 2003/0014082 A1 * | 1/2003 | Schu et al. ............... 607/5 |
| 2004/0133247 A1 * | 7/2004 | Stahmann et al. ........ 607/17 |

* cited by examiner

*Primary Examiner*—Jean Bruner Jeanglaude
(74) *Attorney, Agent, or Firm*—Daniel G. Chapik

(57) ABSTRACT

An implantable medical device uses a sampling scheme to obtain digital representation from analog signals. The analog signals represent intracardiac activity. Generally, a detector detects the amplitude of the analog signals and generates first and second difference signals. The first difference signal is generated after detection of significant changes in the analog signal amplitude. The second difference signal is generated upon confirmation of the absence of significant changes in the analog signal amplitude over a predetermined period of time. A frequency selection is implemented to select the sampling frequency based on the first and second difference signal.

21 Claims, 10 Drawing Sheets

DSP WITH VARIABLE SAMPLE FREQUENCY

FIELD

Most embodiments in this disclosure relate to systems for sampling analog signals, and in particular physiologic signals such as cardiac signals, so as to achieve efficient data compression with relatively little data loss, and minimum energy consumption for sampling of the signals.

BACKGROUND

As a result of significant technological advances over the past decade, implantable medical devices (IMDs) can now be equipped with processing circuitry and memories for storing episodes of digitized physiological signals. For example, a pacemaker may be designed to perform the task of sensing, digitizing, and storing intracardiac signals for later uploading to an external device. The pacemaker need not be restricted to acquiring cardiac signals, but can also be used for obtaining, digitizing, and storing sensor signals, e.g., pressure sensor signals. Such signals are conventionally continuously sampled at a high rate in order to capture the highest anticipated or relevant frequency, such as those which occur during the actual contraction of the heart. For physiological heart signals, the importance is to be able to measure the amplitude of a signal during a contraction accurately. Typically, during cardiac contraction, the signals contain much more high frequency components compared to the situation between two contractions. This means that when the high frequencies are left out (which happens when the signal is sampled at a too low frequency), the amplitude is measured inaccurately. Examples of systems already in use which obtain and store digitized physiological signals are pacemakers, cardioverter defibrillator units and implantable hemodynamic monitors.

In IMDs, the task of digitizing data for storage and transmission to an external receiver becomes difficult because of the need to conserve data processing time and power. Generally available memory is a limitation, but even where the memory limitation is not significant, a data compression scheme is needed to save power during the data processing, telemetry communication, and the sampling process. It is known that data compression techniques can be used in order to increase the amount of signal information available for storage in available memory. See, for example, commonly assigned pending U.S. application Ser. No. 08/561,738, P-3432, "System and Method for Compressing Digitized Signals in Implantable and Battery-Powered Devices," filed Nov. 22, 1995.

Because of the limited availability of processing resources and power, compression techniques for IMDs need to focus on achieving the greatest degree of data compression within the confines of allowable information loss. Thus, some lossy compression can be utilized in IMDs, to reach higher compression ratios with limited signal distortion.

SUMMARY

Analog physiological signals such as cardiac signals are represented digitally using a sampling scheme that conserves energy while enabling a high level of data compression at minimized information loss. Specifically, analog signals representing intracardiac activity are detected with differential signals derived from changes in the analog signal amplitudes. Stability in the analog signal amplitudes is determined over a period of time to select an effective sampling frequency for digital representation.

DRAWINGS

DESCRIPTION OF VARIOUS EMBODIMENTS

Figure 1A:
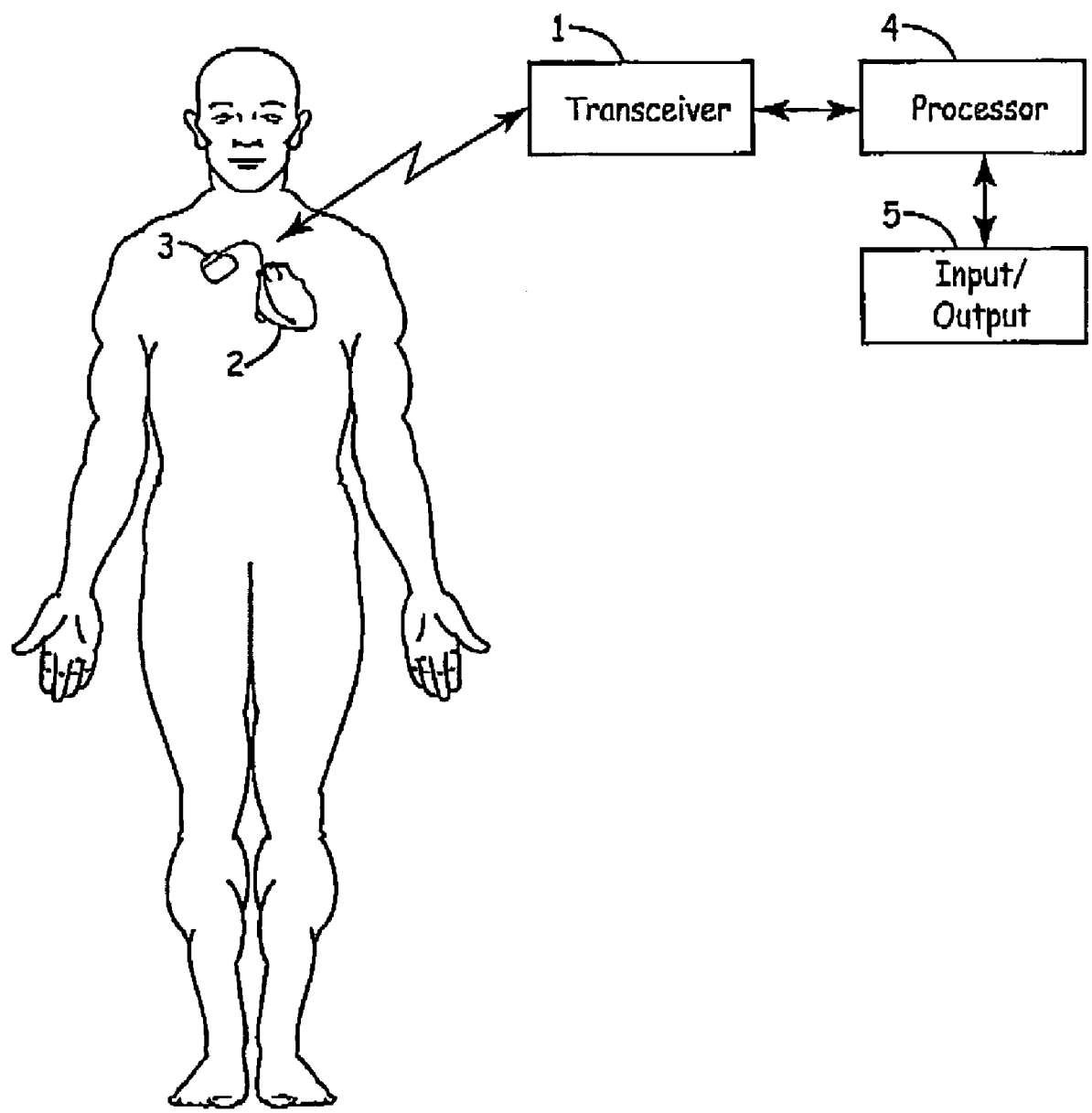
FIG. 1 shows an implanted device such as a pacemaker in an embodiment of the present invention.

The following discussion is presented to enable a person skilled in the art to make and use embodiments of the invention. Various modifications to the illustrated embodiments will be readily apparent to those skilled in the art, and the generic principles herein may be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention. The following introductory material is intended to familiarize the reader with the general nature and some of the features of embodiments of the invention. While the invention is discussed in relation to a pacemaker, it is fully contemplated the invention could be extended to other implantable devices, such as a defibrillator, without departing from the spirit of the invention.

A system constructed and operated according to the embodiments of the invention that may be used to deliver the therapies discussed above may include a signal generator, timing circuit, and/or microprocessor control circuit of the type included in existing pacemaker, IMDs are known in the art. Exemplary systems are shown in U.S. Pat. Nos. 5,158,078, 5,318,593, 5,226,513, 5,314,448, 5,366,485, 5,713,924, 5,224,475 and 5,835,975 each of which is incorporated herein by reference, although any other type of implantable pacemaker or cardioverter defibrillator may be used for this purpose. In such systems, EGM sensing is performed by electrodes carried on leads placed within the chambers of the heart, and/or on the housing of the device. Alternatively, subcutaneous and/or external pad or patch electrodes may be used to sense cardiac signals. Physiological sensors may likewise be carried on device housings or lead systems according to any of the configurations and/or sensing systems known in the art.

All embodiments of the invention share a common electrode configuration to deliver electrical stimulation energy where necessary and to time the delivery of this energy to achieve beneficial effects while avoiding unsafe delivery (as further described hereinbelow). For each therapy component described above, specific electrode locations and geometries may be preferred. The locations for the electrodes of these embodiments of the invention for stimulation include: use of large surface area defibrillation coil electrodes in the heart or adjacent to the heart; pacing electrodes at locations including RV apex, outflow tract, atrial locations, HIS bundle site, left side epicardium, pericardial surface of the heart or endocardium; transthoracic electrodes including paddles and patches, can electrode, temporary electrodes (e.g., epicardial, transvenous or post-operative electrodes), subcutaneous electrodes and multiple site stimulation.

In accordance with common biomedical engineering practices, stimulation therapy is applied with minimized net charge delivery to reduce corrosion and counteract polarization energy losses. Both energy efficient therapy delivery and electrogram (EGM) sensing benefit from low polarization lead systems. Further, the electrodes are preferably connected to fast recovery amplifiers that allow EGM sensing soon after therapy delivery.

The most fundamental sensors are those based on electrograms (ECG or EGMs) and reflect cardiac electrical activity. These sensors require electrodes located where they can readily detect depolarization and repolarization signals as well as sense amplifiers for the monitoring of heart rhythm and diagnosis of arrhythmias.

Electrocardiogram (ECG) or electrogram (EGM) signals from electrodes within the patient's body may be used to detect dysfunction and heart failure (HF). For example, the ST segment level of a cardiac cycle (PQRST) detected by an ECG may be monitored. An elevated or depressed ST segment level has been found to be a reliable indicator of ischemia, a condition known to be associated with dysfunction and HF. Alternatively, the duration of the Q-T interval may also be used to detect hemodynamic dysfunction. For example, a shortened Q-T interval may indicate myocardial dysfunction. A template matching algorithm such as a wavelet classification algorithm may be used to identify electrogram signals that are associated with hemodynamic dysfunction.

Referring now to FIG. 1, a diagram is shown illustrating the environment of the apparatus and method of the invention. The invention may be used with an implantable device such as a pacemaker 3, illustrated as implanted in a patient. Connected to the pacemaker is a lead 2, which extends into the patient heart, and has one or more electrodes at the distal end thereof which deliver stimulus pulses and also sense cardiac signals. As is well known in the pacemaker art, the sense signals can be received by the pacemaker, digitized and stored in memory, for later transmission to an external device; alternately, they can be down-loaded directly to an external programmer device. Likewise, one or more sensors located on the lead or in the pacemaker can produce the signals which are to be digitized and stored. As shown, the transceiver 1 may be a conventional programmer as used in the pacemaker art. The programmer, when it has received data from the pacemaker, can transfer it to a processor 4, which in turn can output data to input/output device 5, all in a well known manner.

Figure 2:
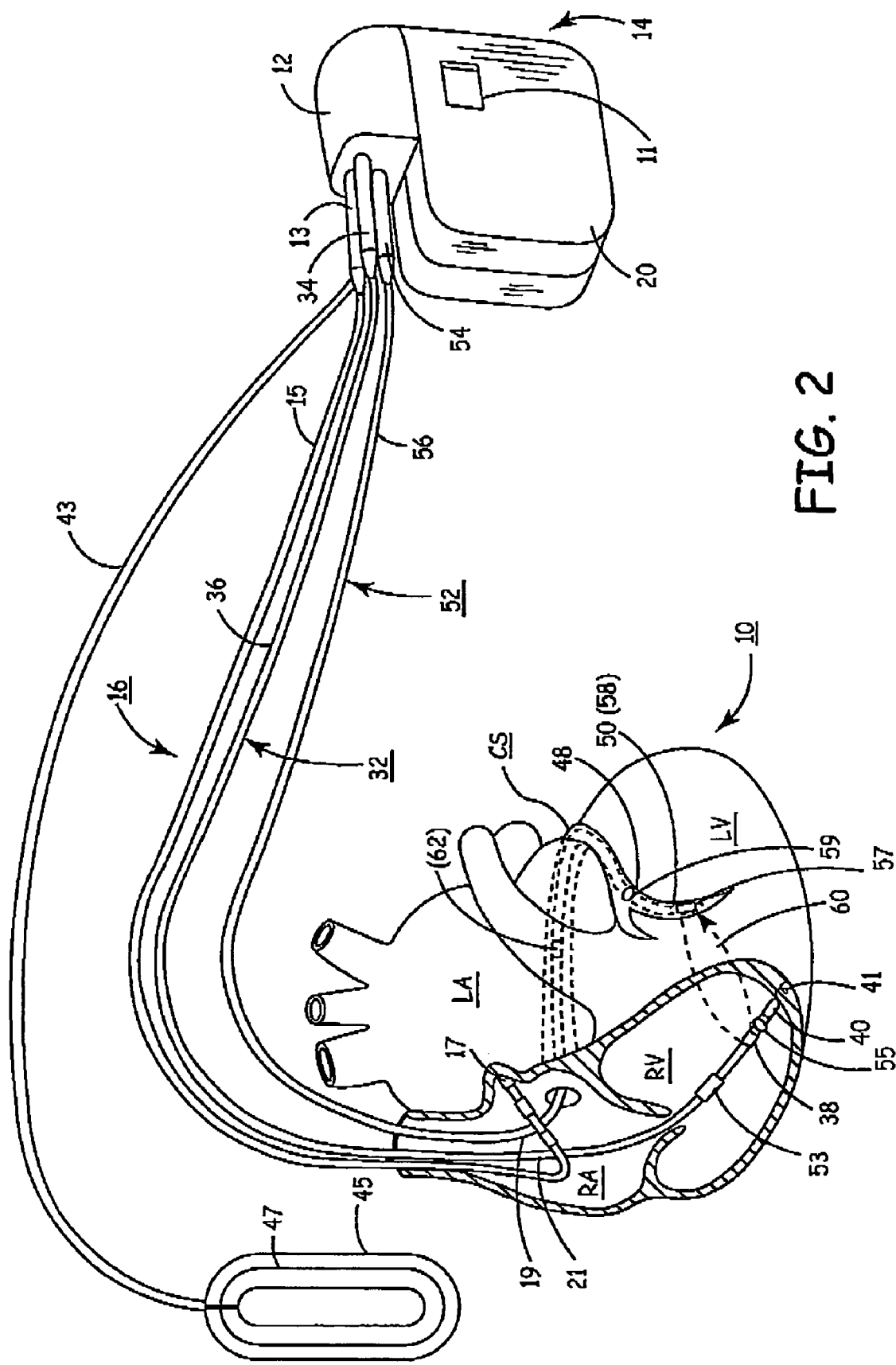
FIG. 2 is a schematic diagram depicting a multi-channel, atrial and bi-ventricular, monitoring/pacing implantable medical device (IMD) in which the embodiments of the invention is preferably implemented.

In FIG. 2, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein that extends further inferiorly into branches of the great vein. The cardiac cycle commences normally with the generation of the depolarization impulse at the SA Node in the right atrial wall. The impulse then conducts through the right atrium, and conducts to the left atrial septum by way of Bachmann's bundle. The RA depolarization wave reaches the atrio-ventricular (AV) node and the atrial septum within about 40 msec and reaches the furthest walls of the RA and LA within about 70 msec. Approximately 50 ms following electrical activation, the atria contract. The aggregate RA and LA depolarization wave appears as the P-wave of the PQRST complex when sensed across external ECG electrodes and displayed. The component of the atrial depolarization wave passing in proximity to a unipolar or pair of bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node conducts down the bundle of His in the intraventricular septum after a delay of about 120 msec. The depolarization wave reaches the apical region of the heart about 20 msec later and then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing by a bipolar or unipolar pace/sense electrode pair located on or adjacent to the myocardium exceeds a threshold amplitude, it is detected as a sensed R-wave. Although the location and spacing of the external ECG electrodes or implanted unipolar ventricular pace/sense electrodes has some influence on R-wave sensing, the normal R-wave duration does not exceed 80 msec as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The normal electrical activation sequence can become highly disrupted in patients suffering from advanced HF and can manifest itself as an intra-atrial conduction delay (IACD), left bundle branch block (LBBB), right bundle branch block (RBBB), and/or intraventricular conduction delay (IVCD). These conduction defects give rise to dyssynchrony between RV and LV activation as well as intraventricular dyssynchrony. In RBBB and LBBB patients, the QRS complex is widened beyond the normal range to between 120 msec and 250 msec as measured on surface ECG. This increased width demonstrates the lack of synchrony of the right and left ventricular depolarizations which is often linked to dyssynchronous contraction.

FIG. 2 also depicts an implanted, multi-channel cardiac pacemaker, ICD, IPG (implantable pulse generator) or other IMD of the above noted types for restoring AV synchronous contractions of the atrial and ventricular chambers and simultaneous or sequential pacing of the right and left ventricles. The pacemaker IPG 14 is implanted subcutaneously in a patient's body. Up to three endocardial leads 16, 32, and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiority in a branching vessel of the great vein 48 to extend the distal LV CS pace/sense electrode 50 alongside the LV chamber. The distal end of such LV CS leads is advanced through the superior vena cava, the right atrium, the ostium of the coronary sinus, the coronary sinus, and into a coronary vein descending from the coronary sinus, such as the great vein. Typically, LV CS leads and LA CS leads do not employ any fixation mechanism and instead rely on the close confinement within these vessels to maintain the pace/sense electrode or electrodes at a desired site. The LV CS lead 52 is formed with a small diameter single conductor lead body 56 coupled at the proximal end connector 54 fitting into a bore of IPG connector block 12. A small diameter unipolar lead body 56 is selected in order to lodge the distal LV CS pace/sense electrode 50 deeply in a vein branching inferiority from the great vein 48.

Preferably, the distal, LV CS active pace/sense electrode 50 is paired with the proximal RV defibrillator coil 53 or can 20 for delivering LV pace pulses. The distal LV CS active pace/sense electrode 50 is also preferably paired with the distal tip RV active pace/sense electrode 40 for sensing across the RV and LV as described further below.

Moreover, in a four-chamber embodiment, LV CS lead 52 could additionally bear a proximal LA CS pace/sense electrode positioned along the lead body to lie in the larger diameter coronary sinus CS adjacent the LA. In that case, the lead body 56 would encase two electrically insulated lead conductors extending proximally from the more proximal LA CS pace/sense electrode(s) and terminating in a bipolar connector 54. The LV CS lead body may also be smaller between the proximal LA CS electrode and the distal LV CS active pace/sense electrode 50. RA pacing and sensing could occur between electrode 17 and housing 20.

Typically, in pacing/defibrillation systems of the type illustrated in FIG. 2, the electrodes designated above as "pace/sense" electrodes are used for both pacing and sensing functions. In accordance with one aspect of the embodiments of the invention, these "pace/sense" electrodes can be selected to be used exclusively as pace or sense electrodes or to be used in common as pace/sense electrodes in programmed combinations for sensing cardiac signals and delivering pace pulses along pacing and sensing vectors. Separate or shared indifferent pace and sense electrodes can also be designated in pacing and sensing functions. For convenience, the following description separately designates pace and sense electrode pairs where a distinction is appropriate. With respect to the embodiments of the invention, a subcutaneous electrode 45 coupled to medical electrical lead 43 may be added to or substituted for one or more of the leads or electrodes depicted in FIG. 2. If a subcutaneous electrode 45 is utilized, a suitable defibrillation coil 47 may be coupled to appropriate high voltage circuitry to deliver a timed defibrillation pulse. While coil electrode 53 is depicted coupled to a portion of RV lead 32, such an electrode may be coupled to other portions of any of the leads depicted in FIG. 2, such as LV electrode 57. The coil electrode 53, subcutaneous electrode 45 or other types of suitable electrode configurations may be electrically coupled to low voltage pacing/sensing circuitry in addition to high voltage circuitry. As is known, such electrodes may be disposed in a variety of locations in, around, and on the heart.

Also depicted in FIG. 2 is an RV sensor 55 and an LV sensor 59 which may comprise one or more of a variety of sensors as is known in the art. Preferably RV sensor 55 comprises an absolute pressure sensor, but other pressure sensors may be utilized. In addition, RV sensor 55 may comprise an accelerometer, an impedance electrode, a saturated oxygen sensor, a pH sensor, and the like. In addition, each of the leads could carry a mechanical sensor for developing systolic and diastolic pressures and a series of spaced apart impedance sensing leads for developing volumetric measurements of the expansion and contraction of the RA, LA, RV and LV.

Of course, such sensors must be rendered biocompatible and reliable for long-term use. In addition, one or more sensors may be disposed in or on the housing 20 of IMD 14 such as sensor 11 depicted in FIG. 2.

Figure 3A:
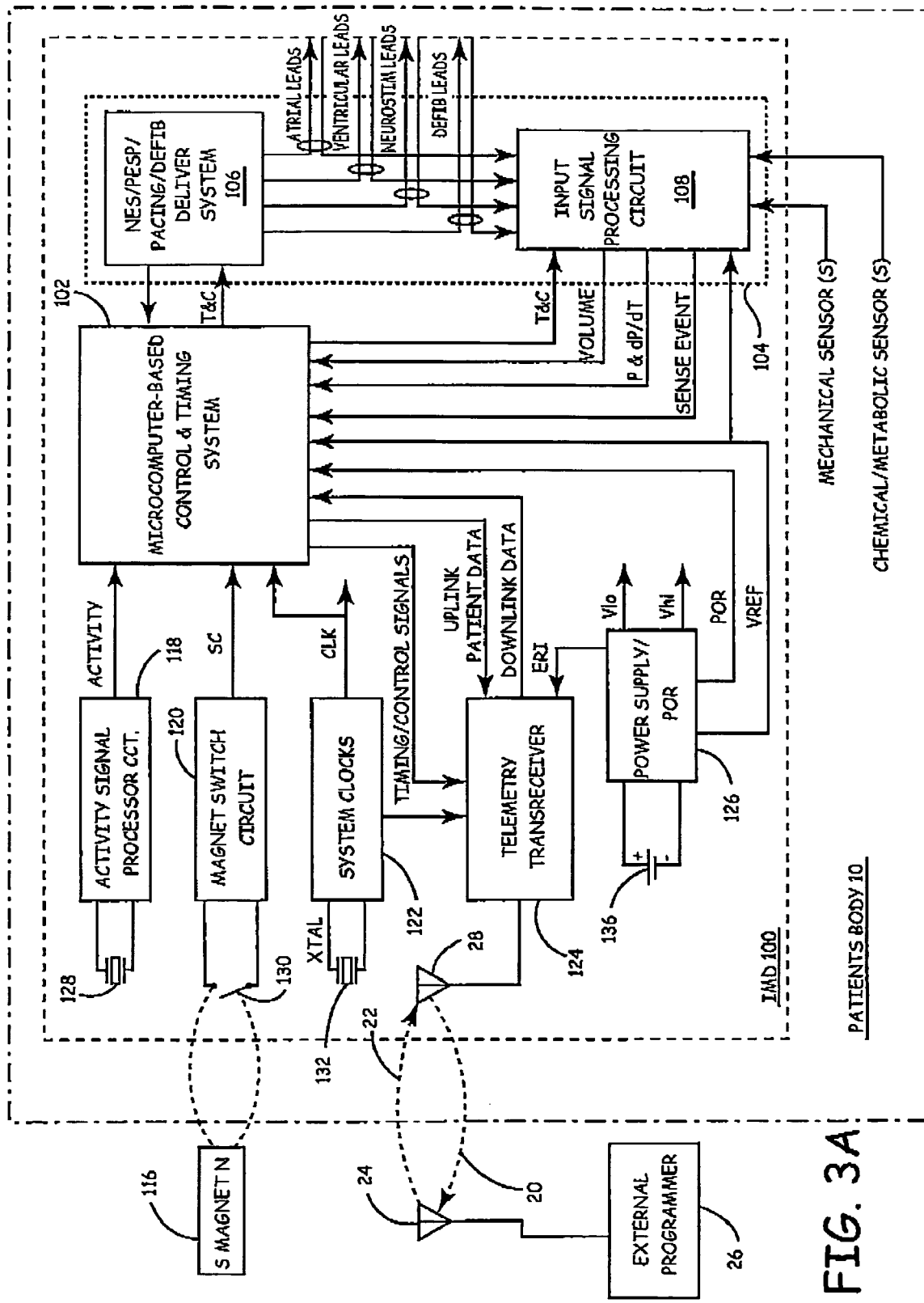
FIG. 3A is a simplified block diagram of one embodiment of IPG circuitry and associated leads employed in the system of FIG. 2 enabling therapy delivery and heart failure state monitoring in one or more heart chambers.

FIG. 3A depicts a system architecture of an exemplary multi-chamber IMD 100 implanted into a patient's body 10 that provides delivery of a therapy and/or physiologic input signal processing. The typical multi-chamber monitor/sensor 100 has a system architecture that is constructed about a microcomputer-based control and timing system 102 that varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU, ALU, etc., of a typical microprocessor core architecture. Of course, such firmware and software may be modified in situ (e.g., in vivo) and the operational characteristics may be adapted for a particular situation or patient. A physician or clinician may change one or more parameters which will cause a change in the detection or response of such algorithms. Oftentimes, discrete values may be changed such that a desired software routine is advantageously altered, although sometimes an entirely new set of operating software may be substituted for an existing set of operating software, as is known in the art. The microcomputer-based multi-chamber monitor/sensor control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor 100 can be accomplished with dedicated circuit hardware or state machine logic rather than a programmed micro-computer.

The multi-chamber monitor/sensor 100 also typically includes patient interface circuitry 104 for receiving signals from sensors and pace/sense electrodes located at specific sites of the patient's heart chambers and/or delivering stimulation to derive heart failure parameters or a pacing therapy to the heart chambers. The patient interface circuitry 104 therefore comprises a stimulation delivery system 106 optionally including pacing and other stimulation therapies and a physiologic input signal processing circuit 108 for processing the blood pressure and volumetric signals output by sensors. For purposes of illustration of the possible uses of these embodiments of the invention, a set of lead connections are depicted for making electrical connections between the therapy delivery system 106 and the input signal processing circuit 108 and sets of pace/sense electrodes located in operative relation to the RA, LA, RV and LV.

As depicted in FIG. 3A, chemical/metabolic sensor input and/or mechanical sensor inputs are provided to the input signal processing circuit 108. As described with respect to FIG. 2, a wide variety of such sensors may be utilized when practicing the embodiments of the invention.

A battery provides a source of electrical energy to power the multi-chamber monitor/sensor operating system including the circuitry of multi-chamber monitor/sensor 100 and to power any electromechanical devices, e.g., valves, pumps, etc. of a substance delivery multi-chamber monitor/sensor, or to provide electrical stimulation energy of an ICD shock generator, cardiac pacing pulse generator, or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106.

Virtually all current electronic multi-chamber monitor/sensor circuitry employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 3A, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers may be used for storing data compiled from sensed cardiac activity and/or relating to device operating history or sensed physiologic parameters for uplink telemetry transmission on receipt of a retrieval or interrogation instruction via a downlink telemetry transmission. The criteria for triggering data storage can also be programmed in via downlink telemetry transmitted instructions and parameter values. The data storage is either triggered on a periodic basis or by detection logic within the physiologic input signal processing circuit 108 upon satisfaction of certain programmed-in event detection criteria. In some cases, the multi-chamber monitor/sensor 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted multi-chamber monitor/sensor 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later interrogation session.

In the multi-chamber monitor/sensor 100, uplink and downlink telemetry capabilities are provided to enable communication with either a remotely located external medical device or a more proximal medical device on the patient's body or another multi-chamber monitor/sensor in the patient's body as described above with respect to FIG. 2 and FIG. 3A (and FIG. 3B described below). The stored physiologic data of the types described above as well as real-time generated physiologic data and non-physiologic data can be transmitted by uplink RF telemetry from the multi-chamber monitor/sensor 100 to the external programmer or other remote medical device 26 in response to a downlink telemetered interrogation command. The real-time physiologic data typically includes sampled signal waveforms (e.g. intracardiac EGM or pressure waveforms), waveform derived parameters (e.g. $dP/dt_{max}$ or intracardiac electrocardiogram amplitude values), and sensor output signals. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/sensor thus develops a variety of such real-time or stored, physiologic or non-physiologic, data, and such developed data is collectively referred to herein as "patient data."

The physiologic input signal processing circuit 108 therefore includes at least one electrical signal amplifier circuit for amplifying, processing and in some cases detecting sense events from characteristics of the electrical sense signal or sensor output signal. The physiologic input signal processing circuit 108 in multi-chamber monitor/sensors providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave, R-wave, or T-wave respectively and providing an ASENSE, VSENSE or TSENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in a variety of ways known in the art.

In addition, the input signal processing circuit 108 includes at least one physiologic sensor signal processing channel for sensing and processing a sensor derived signal from a physiologic sensor located in relation to a heart chamber or elsewhere in the body.

Figure 3B:
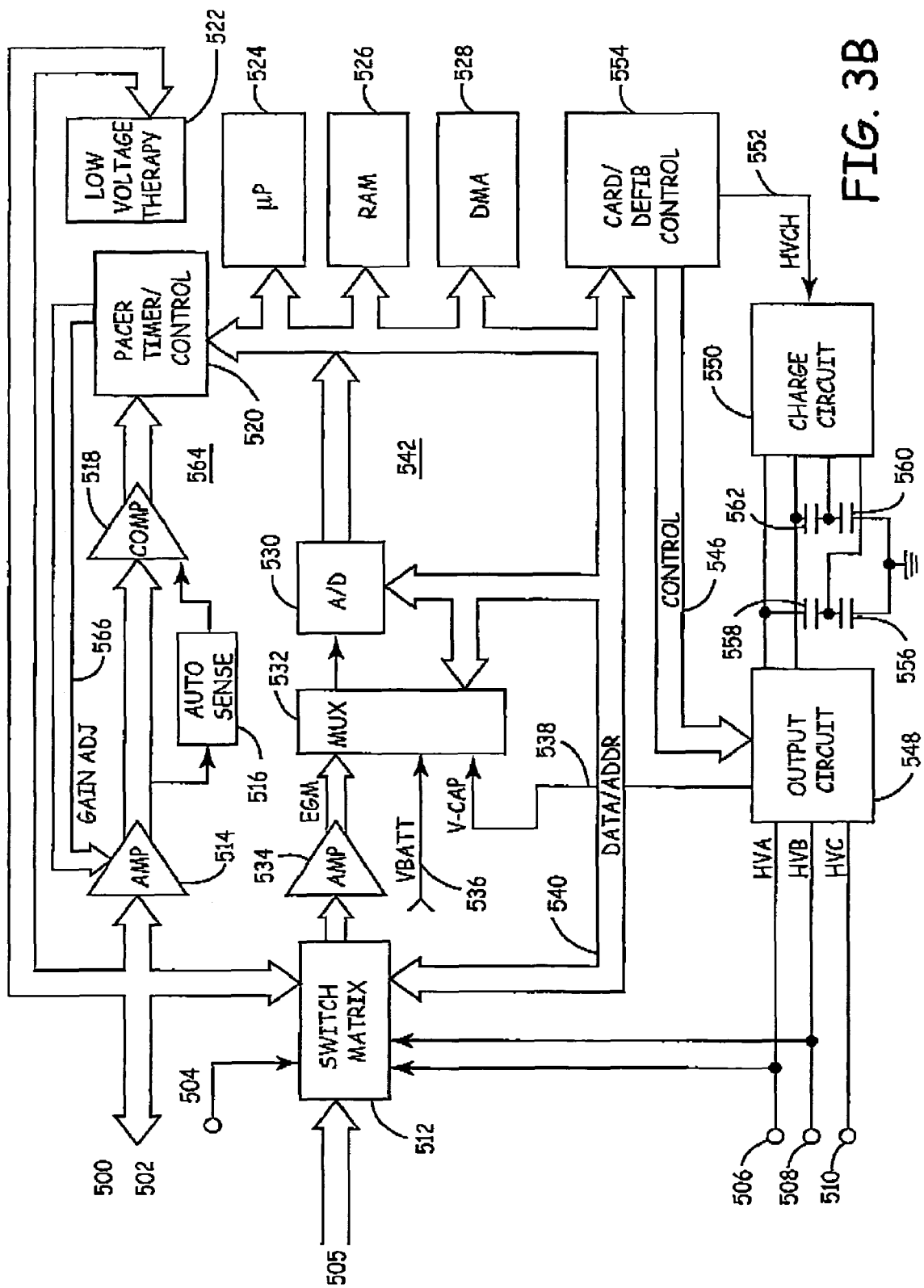
FIG. 3B, is a simplified block diagram of another embodiment of IPG circuitry and associated leads that can be employed in the system of FIG. 2 enabling therapy delivery and heart failure state monitoring in one or more heart chambers.

Now turning to FIG. 3B, another system architecture for use in conjunction with the embodiments of the invention is depicted. FIG. 3B is an exemplary system that may be utilized to deliver therapy by incorporating the system and method described above. Notably, the depicted system includes a sense amplifier 534 to sense electrical signals such as EGM signals using one or more leads placed within a respective chamber of the heart. One or more physiological or hemodynamic signals may be sensed using sensors such as those discussed above. These additional signals, which are shown collectively provided on line 505, may be used to determine cardiac output so that therapy may be initiated, terminated, and/or optimized.

The system of FIG. 3B further includes a timer/controller to control the delivery of pacing pulses on output lines 500 and 502. This circuit, alone or in conjunction with microprocessor 524, controls interval lengths, pulse amplitudes, pulse lengths, and other waveform attributes associated with the pulses. Output circuit 548 delivers high-voltage stimulation such as defibrillation shocks under the control of defibrillation control circuit 554.

Not all of the conventional interconnections of these voltages and signals are shown in either FIG. 3A or FIG. 3B and many other variations on the illustrated electronic circuitry are possible, as is known to those of skill in the art.

Figure 4:
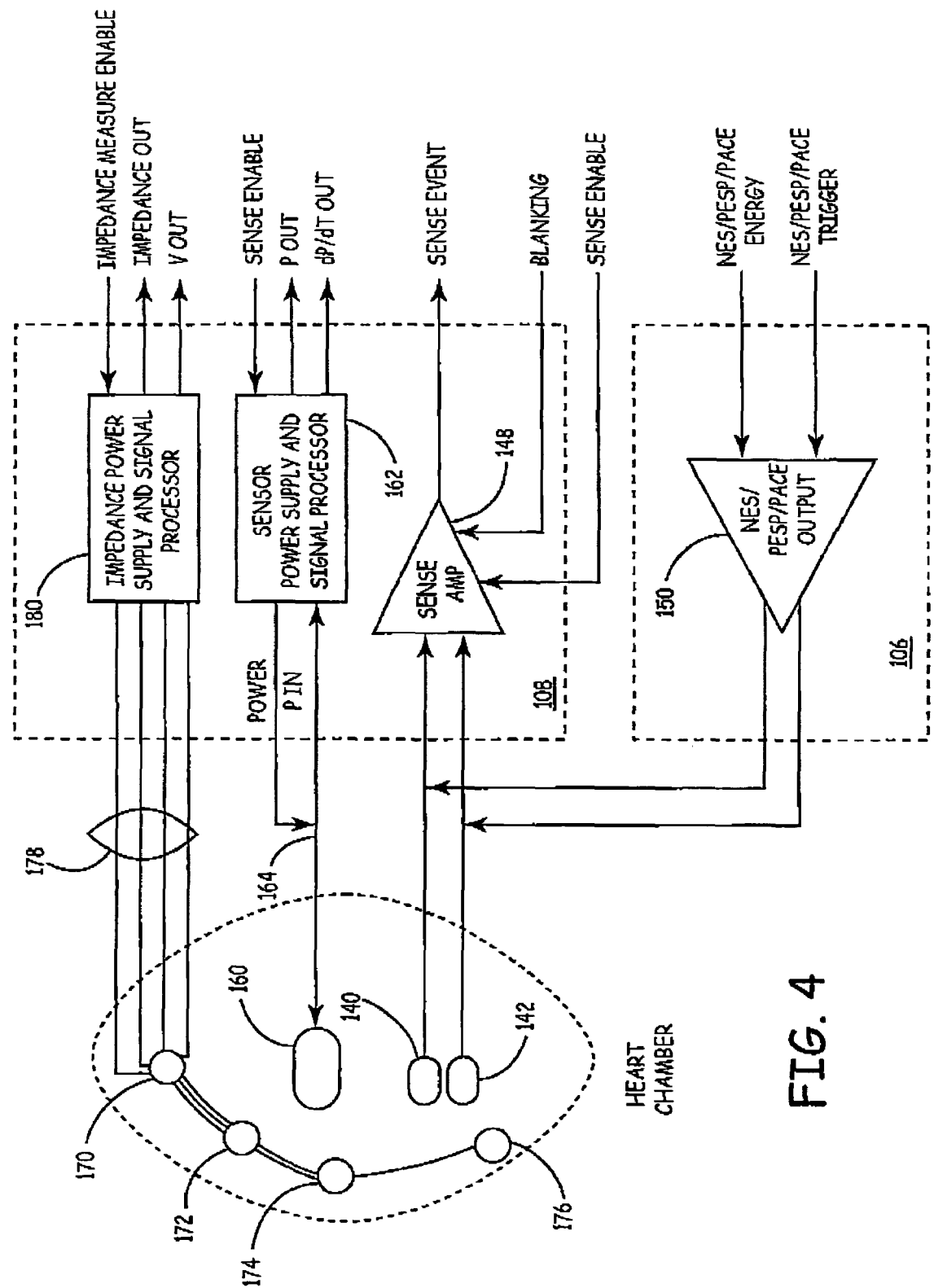
FIG. 4 is a simplified block diagram of a single monitoring and pacing channel for deriving pressure, impedance and cardiac EGM (electrogram) signals employed in monitoring heart failure and optionally pacing the heart and delivering therapy in accordance with the embodiments of the invention.

FIG. 4 schematically illustrates one pacing, sensing, and parameter measuring channel in relation to one heart chamber. A pair of pace/sense electrodes 140,142, a sensor 160, and a plurality, e.g., four, impedance measuring electrodes 170,172,174,176 are located in operative relation to the heart chamber. The pair of pace/sense electrodes 140, 142 are located in operative relation to the heart chamber and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled as described below in reference to the measurement of the parameters of heart failure. The blanking signal is provided by control and timing system 102 upon delivery of a pacing pulse or pulse train to disconnect the sense amplifier inputs from the lead conductors 144 and 146 for a short blanking period in a manner well known in the art. When sense amplifier 148 is enabled and is not blanked, it senses the electrical signals of the heart, referred to as the EGM, in the heart chamber. The sense amplifier provides a sense event signal signifying the contraction of the heart chamber commencing a heart cycle based upon characteristics of the EGM, typically the P-wave when the heart chamber is the RA or LA and the R-wave, when the heart chamber is the RV or LV, in a manner well known in the pacing art. The control and timing system responds to non-refractory sense events by restarting an escape interval (EI) timer timing out the EI for the heart chamber, in a manner well known in the pacing art.

The pair of pace/sense electrodes 140, 142 are also coupled through lead conductors 144 and 146, respectively, to the output of a pulse generator 150. The pulse generator 150, within pacing delivery system 106, selectively provides a pacing pulse to electrodes 140, 142 in response to a PACE trigger signal generated at the timing system 102 in a manner well known in the pacing art.

The sensor 160 and/or other physiologic sensor is coupled to a sensor power supply and signal processor 162 within the input signal processing circuit 108 through a set of lead conductors 164 that convey power to the sensor 160 to the sensor power supply and signal processor 162. The sensor power supply and signal processor 162 samples the blood pressure impinging upon a transducer surface of the sensor 160 located within the heart chamber when enabled by a sense enable signal from the control and timing system 102. As an example, absolute pressure P, developed pressure DP and pressure rate of change dP/dt sample values can be developed by sensor power supply and signal processor unit 162 or by the control and timing system 102 for storage and processing as described further below. The sensor 160 and a sensor power supply and signal processor 162 may take the form disclosed in commonly assigned U.S. Pat. No. 5,564, 434, incorporated herein by reference, in relevant parts.

The set of impedance electrodes 170, 172, 174 and 176 is coupled by a set of conductors 178 and is formed as a lead of the type described in the above-referenced '717 patent that is coupled to the impedance power supply and signal processor 180. Impedance-based measurements of cardiac parameters such as stroke volume are known in the art. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

In accordance with the embodiments of the invention, the IMD measures a group of parameters indicative of the state of heart failure employing EGM signals, measures of absolute blood pressure P and/or dP/dt, saturated oxygen, flow, pH or the like and measures of heart chamber volume V over one or more cardiac cycles.

Some aspects of the present invention include: Adaptability for application at the sampling stage of the signal flow. The decision-circuitry that determines which sample frequency must be used can be implemented without the need for difficult control mechanisms. Utilizing the present invention at the sampling stage means that no energy is wasted for taking samples that would be discarded when a compression algorithm is applied after sampling. Further, the frequency of sampling is known and fixed. While exotic digital filter designs might be able to handle the variation in sample-frequency this will be at the cost of processing power, which is undesirable.

Figure 5:
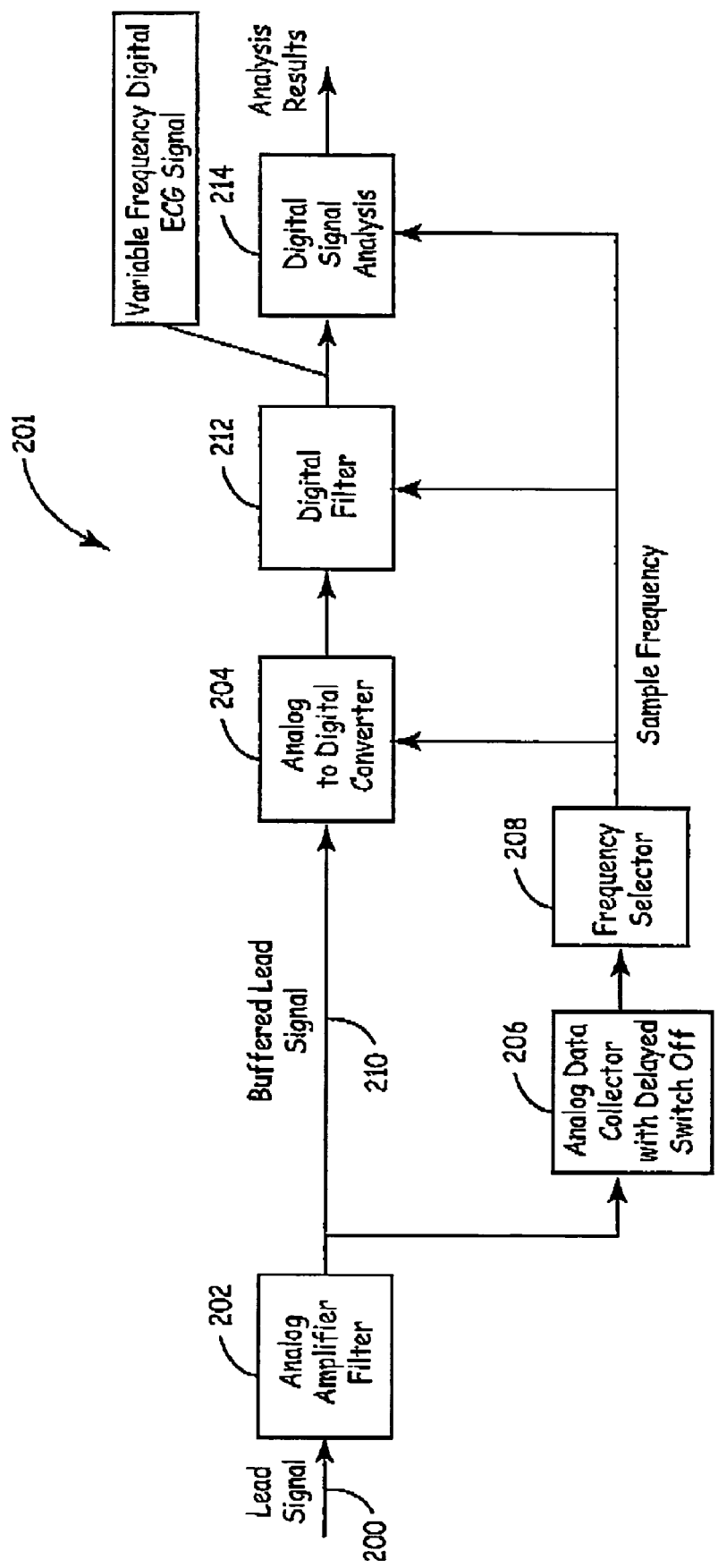
FIG. 5 is a simplified block diagram of an implementation of a system for DSP with variable sample frequency in an embodiment of the present invention.

With respect to FIG. 5, a simplified block diagram of an implementation of a system for DSP with variable sample frequency in an embodiment of the present invention is shown. The implementation of FIG. 5 would generally occur within input signal processing circuit 108 where lead signal 200 is inputted within analog amplifier filter 202. Filter 202 acts as a common band pass filter to eliminate unwanted frequency components above 400 Hz and below 4 Hz which is the common frequency range for an ECG or EGM. The filtered signal then continues on to an analog to digital converter 204 and an analog delta detector 206. Delta detector 206 is utilized to detect changes in signal amplitude above a predetermined limit. The manufacturer or the physician could set this predetermined limit during device implantation, regardless; the limit would be used to detect a significant change in the signal and thus a need to increase the sampling rate. As is well know, the higher the sampling rate, the better signal identification and reproduction. For purposes of the disclosure, the predetermined limit is set at approximately 0.2 mV for frequencies above 35 Hz and frequencies below 35 Hz will be covered by the low sample frequency of 100 Hz as discussed below.

Upon detection of a change in amplitude above the predetermined threshold, a signal is generated and sent to frequency selector 208. Upon receiving this signal, frequency selector 208 will increase the frequency, which will correspond to a higher sampling rate for analog to digital converter 204. For purposes of this discussion, the lower frequency limit, or standard sampling rate, is 100 Hz and the upper frequency limit is 800 Hz. However, it is fully contemplated that any frequency range could be utilized including a dynamic frequency range without departing from the spirit of the invention.

Analog signal 200 is first amplified with some minor filtering through filter 202 as discussed above. Amplified signal 210 is then converted into a digital signal, after which it can be digitally filtered in digital filter 212 and analyzed at digital signal analysis block 214. The process of converting, filtering and analyzing can be done at two different sampling rates or dynamically depending on the implementation of frequency selector 208. A high rate, e.g., 800 Hz, allows accurate analysis of details in analog signal 200, and a low rate, e.g., 100 Hz can be used to keep track of the less active parts of analog signal 200.

In pacemakers, for example, the real time analysis of incoming cardiac signals is needed to determine the application of various therapies. Until recently, an analog sense amplifier and its subsequent detection circuitry allowed only for the detection of the occurrence of a cardiac event. The use of digital signal processing also allows for the analysis of morphological aspects of analog signal 200. This dramatically improves the diagnostic value of a pacemaker or defibrillator, since recent research has shown how morphological aspects are related to various pathological states of the heart. However, a limitation of DSP (digital signal processing) is the relatively high energy consumption related to continuous analog to digital conversion of analog signal 200. However, the inventor's have discovered that there is no need to sample analog signal 200 with a constant high sample frequency that is needed for the fastest varying parts of analog signal 200. During a complete heart cycle, there are intervals where the intracardiac signal hardly changes and this would allow for a lower sample frequency while maintaining sufficient quality of the digitized signal. The lowering of the sample frequency consequently leads to a decrease in energy usage, since the dynamic power consumption of DSP is proportional to the applied sampling frequency.

In delta detector 206 significant changes in analog signal 200 are detected and, as discussed above, used as a trigger to use the higher frequency for processing analog signal 200. After a predetermined time frame (e.g., 20 ms) without a change in analog signal 200, the processing frequency can be set to a low frequency again as described above. Other methods of detecting these significant changes in the analog signal can be used, however, a good method for detecting significant changes in analog signal 200 is using threshold detector 206 after the filtered analog signal with the cut off frequency just below the Nyquist frequency of the low sample rate. At the low sample frequency of 100 Hz, only signals with a frequency content below 50 Hz are sampled accurately. Therefore detecting signal content above 50 Hz is a reliable method for choosing between the high and low sample frequency. To compensate for the non-ideal behavior of a simple high pass filter, the cut-off frequency is set somewhat lower, e.g. 35 Hz.

Figure 6:
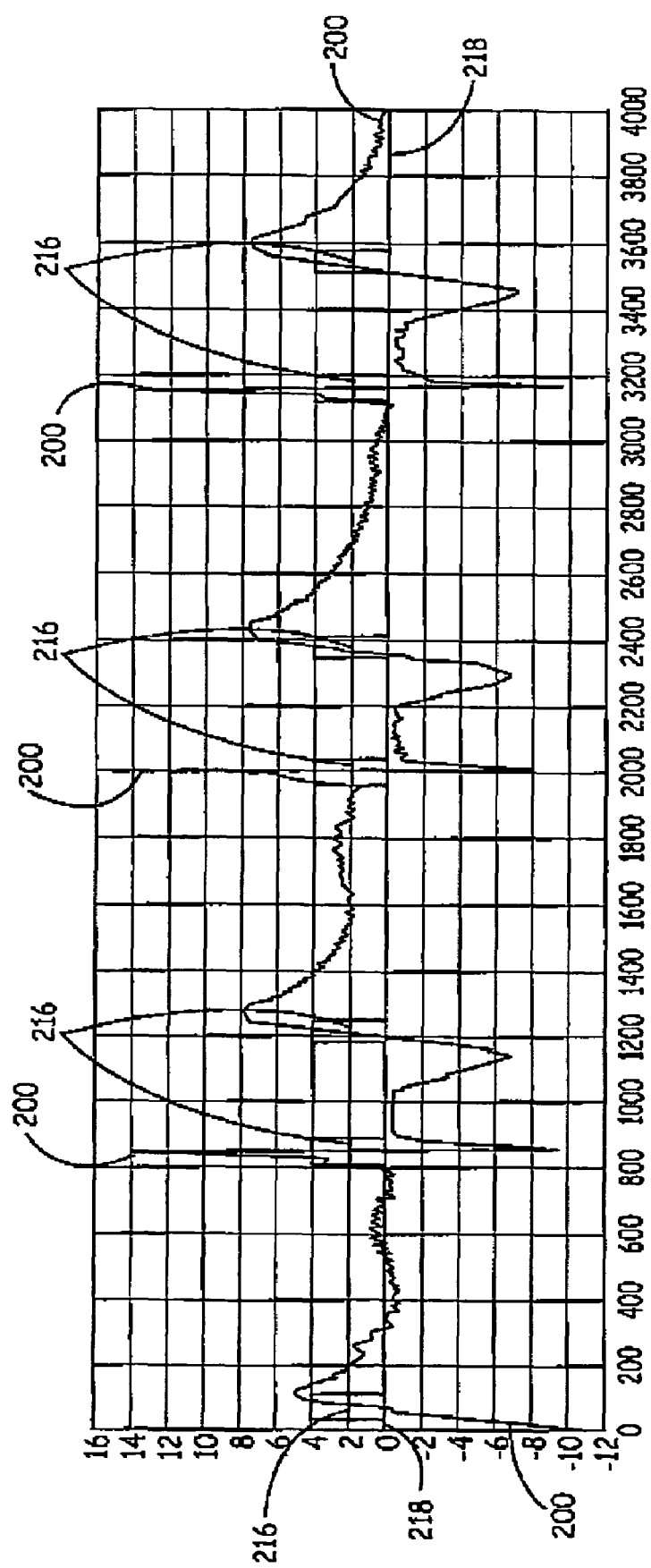
FIG. 6 is a graph of a ECG signal with DSP frequency variations in an embodiment of the present invention.
Figure 7:
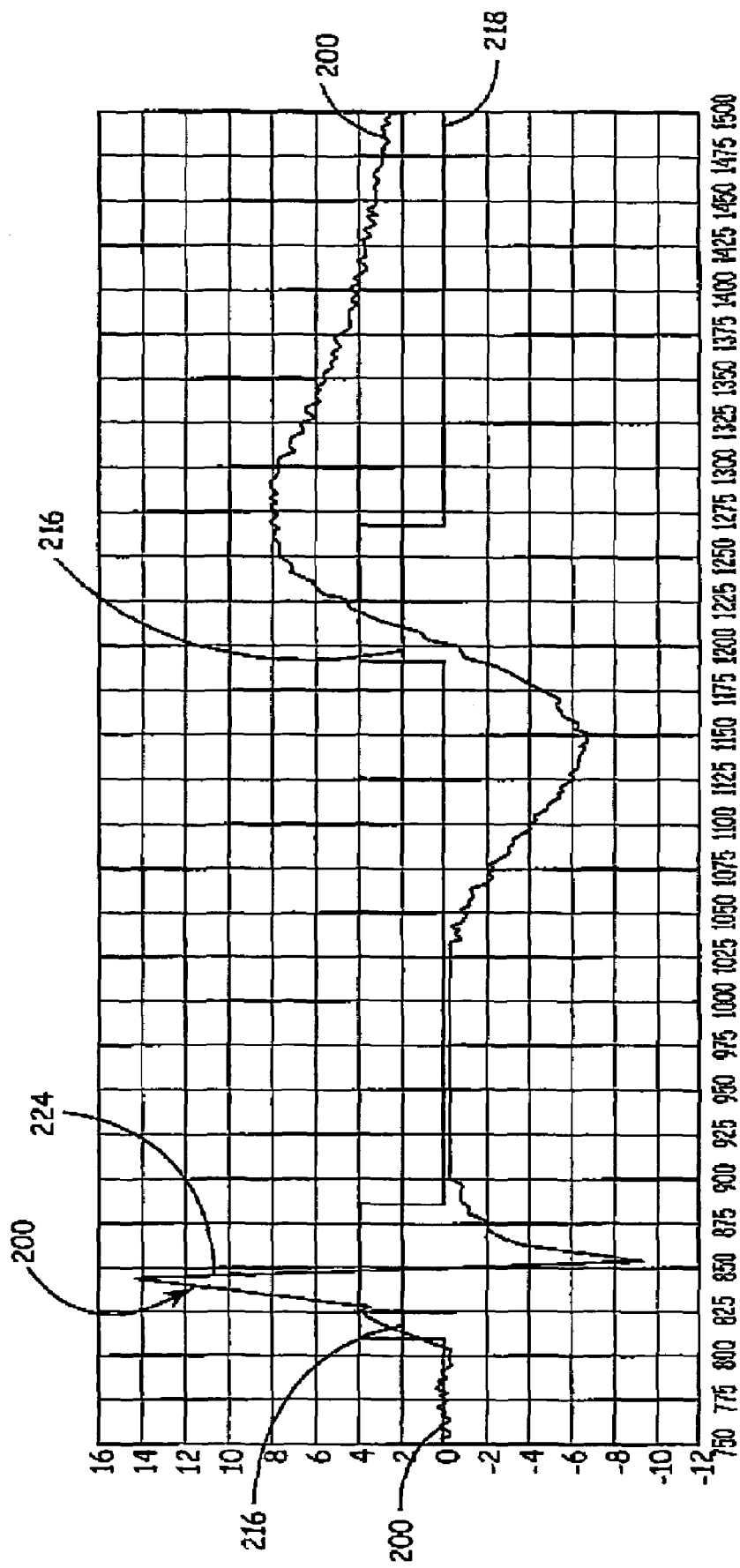
FIG. 7 is a more detailed graph of a ECG signal with DSP frequency variations in an embodiment of the present invention.

With reference to FIGS. 6 and 7, a graph of an ECG signal with DSP frequency variations in an embodiment of the present invention is shown. FIG. 6 is an example of an analog signal 200 processed by the DSP variable frequency sampling system of the present invention. Dots 216 mark the detection of an analog signal with high frequency content (i.e. above 35 Hz) by delta detector 206. Thus a detection of a change in amplitude above the predetermined threshold. Square wave line 218 indicates when the applied sample frequency is high or low. Note that the frequency is kept high for 20 ms when no active signal is detected. This is to prevent the sample frequency from getting low in a less active part of a P or R wave in the QRST waveform.

Figure 8:
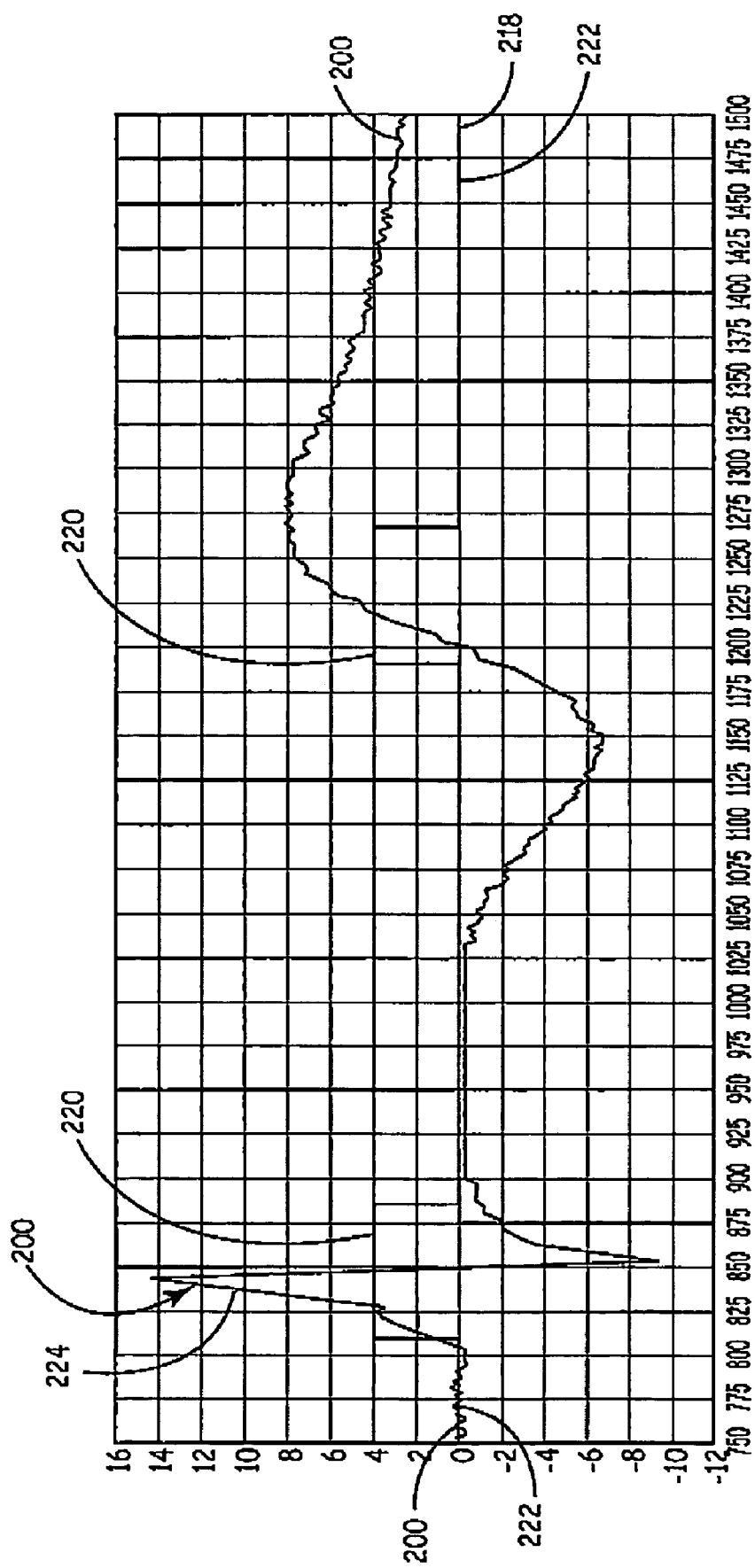
FIG. 8 is an even more detailed graph of an ECG signal with DSP frequency variations in an embodiment of the present invention.

With reference to FIG. 8, an even more detailed graph of an ECG signal with DSP frequency variations in an embodiment of the present invention is shown. In this figure, the result of the variable frequency sampled signal 200 is shown. High portion 220 of signal 218 represents a high frequency sampling rate of 800 Hz and low portion 222 represents a low frequency sampling rate of 100 Hz. As discussed above, the high and low sampling rates can vary and can even be dynamic without departing from the spirit of the invention. However, for purposes of the description 800 and 100 Hz are used. As can be seen, the details of R-wave 224 are preserved more accurately with the higher frequency, while most of the signal is sampled with the lower frequency. The morphology of T-wave is well preserved at the low sampling frequency. In the example, the number of samples is only 22% of the number that would be needed with a fixed sample frequency of 800 Hz. In addition, with minimal additional circuitry, this reduced sample count can also be used as compression for IECG storage and transmission, thereby yielding less samples to process and store.

This method can also be used for compression of IECG storage and transmission without changing the sample-frequency. To accomplish this, the sample-frequency must be set to the high frequency, the frequency determination can be based on the sampled signal (but it is also possible to base it on the analog signal as is described until now). In case the frequency determination indicates that a high frequency is needed (i.e. the signal contains high-frequency components), the samples taken are passed on without further processing. In case the frequency determination indicates that a low frequency can be used (i.e. the signal contains no high-frequency components), only one in every eight samples are passed on for further processing/storage/transmission (one in eight matched the relation between the high and low frequencies: 100 and 800 hertz, and of course these numbers serve just as examples). To be able to reconstruct the compressed signal, it is necessary to know the sample rate of every sample that is stored/transmitted in the compressed form. Two well known methods to accomplish that exist. One is to add a flag to every sample that indicates what its sample frequency was. The second method is to add a unique identifiable marker in the stored/transmitted datastream every time the frequency changes (indication that all following samples until the next marker are sampled at frequency X). The method of choice is dependant on many factors, such as data structure of the samples and that of the store/transmission channel, the expected number of frequency switches, the change of losing the 'frequency indication marker' during transmission, among others.

Basically, system 201 switches between a high and low sampling frequency. However, as stated above, more frequency levels could be included and the system could be able to make a choice between the different levels based on the incoming analog cardiac signal. Upon detection of intervals where the intracardiac signal does not vary much, the sample frequency can be switched to a low frequency. This frequency can be maintained until a significant variation in the intracardiac signal is detected. Hereafter, the sample frequency should be increased to allow thorough analysis of all relevant details of the intracardiac signal. When the start of a new interval of low variation is detected, the sample frequency can be made low again.

Figure 9:
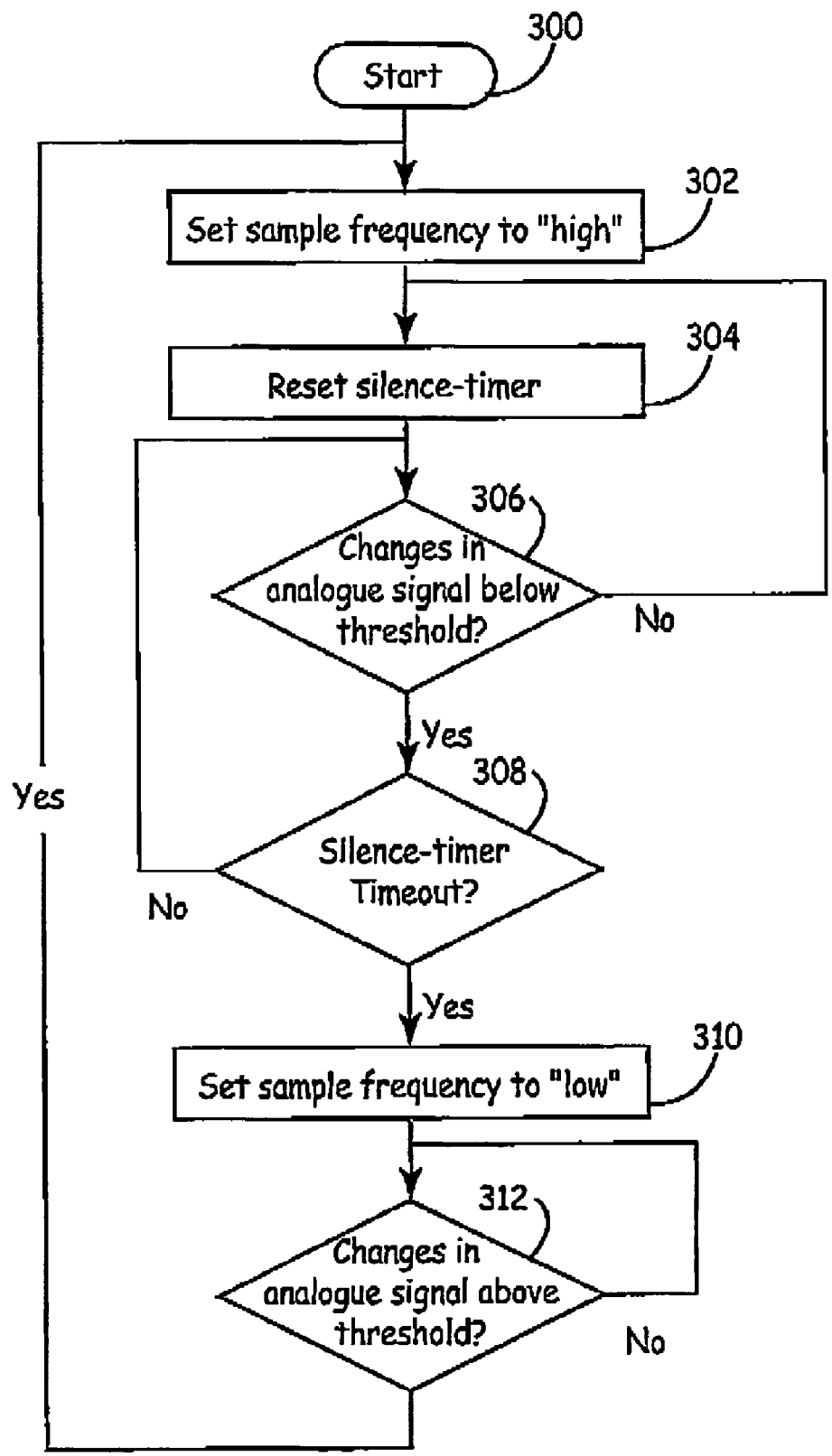
FIG. 9 is a flowchart depiction of a variable frequency-sampling feature in an embodiment of the present invention.

With reference to FIG. 9, a flowchart depiction of a variable frequency-sampling feature in an embodiment of the present invention is shown. State 300 represents initial start up of the implantable device or a possible reset of the system, regardless, upon initial start up of the system; the sampling rate is set to high at stage 302. For this example, the high frequency is 800 Hz; however, as discussed above it could be most any frequency. Further, the initial startup could be at a low frequency; however, it is helpful to have the system in a high sampling rate in case the system starts at an important part of the QRST signal, such as the R wave. Once the frequency is set to high, the silence timer is reset at state 304. The silence timer will begin at the last delta threshold detection and run a predetermined time (e.g., 20 ms) before switching the sampling frequency to a lower limit. During this period, the program is constantly inquiring as to whether the delta value is below a predetermined threshold at state 306. If the delta value is not below a predetermined threshold, the program returns to state 304 to reset the silence timer.

If the delta value is below the threshold, the program advances to determine if the silence timer has timed out at state 308. If the timer has not timed out, the program returns to state 306 to determine if the threshold level has been exceeded. If the timer has timed out, then the program proceeds to state 310 to set the sampling frequency to low, e.g., 100 Hz. The program then proceeds to state 312 where once again the program determines whether the delta value is above the threshold value. If the delta value is not above the threshold value, the program remains at state 312 where it samples analog signal 200 at a low frequency sampling rate. If the delta threshold is exceeded, the program proceeds to state 302 and the high frequency sampling rate begins again. The program then repeats this process to try and obtain the best signal recognition with an optimized energy consumption.

Thus, embodiments of the DSP WITH VARIABLE SAMPLE FREQUENCY are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. An implantable medical device system, comprising:
    sampling means for sampling an analog signal at a sampling frequency to obtain digital representations of the analog signal, the analog signal being representative of intracardiac activity;
    detector means for detecting the amplitude of the analog signal and generating first and second difference signals, the detector means generating the first difference signal after detection of significant changes in the analog signal amplitude, the detector means generating the second difference signal after non-detection of the significant changes in the analog signal amplitude over a predetermined period of time; and
    frequency selector means for selecting the sampling frequency based on the first and second difference signal, the frequency selector means selecting a relatively higher sampling frequency in response to generation of the first difference signal and selecting a relatively lower sampling frequency in response to generation of the second difference signal.

2. The system of claim 1, wherein the significant changes in the signal amplitude include exceeding a predetermined threshold amplitude.

3. The system of claim 1, wherein the detector means includes a threshold detector.

4. The system of claim 1, wherein the higher sampling frequency is 800 Hz.

5. The system of claim 2, wherein the lower sampling frequency is 100 Hz.

6. The system of claim 1, wherein the predetermined period of time is 20 milliseconds.

7. The system of claim 1, wherein the higher sampling frequency is at least double the lower sampling frequency.

8. An intracardiac system for selecting appropriate sampling frequencies of an analog signal representative of intracardiac activity, comprising:
an analog-to-digital converter for converting the analog signal into a digital signal, the analog-to-digital converter sampling the analog signal at a selected sampling frequency;
a threshold detector receiving and analyzing an amplitude of the analog signal, the threshold detector providing indications after a change in the analog signal amplitude exceeds a predetermined threshold amplitude and after a change in the analog signal amplitude fails to exceed the threshold amplitude; and
a frequency selector that sets the selected sampling frequency in response to the threshold detector, the frequency selector setting the selected sampling frequency at a first value in response to the indication that the analog signal amplitude change exceeds a predetermined threshold amplitude, and the frequency selector setting the selected sampling frequency at a second value in response to the indication that the analog signal amplitude change fails to exceed the threshold amplitude over a predetermined amount of time, the first value being higher than the second value.

9. The system of claim 8, wherein the first value has an upper limit of 800 Hz.

10. The system of claim 8, wherein the second value has a lower limit of 100 Hz.

11. The system of claim 8, wherein the predetermined time period is 20 milliseconds.

12. The system of claim 8, wherein the first value is at least double the second value.

13. The system of claim 8, further including a bandpass filter that filters out non-physiological frequency content from the analog signal.

14. The system of claim 8, wherein the frequency selector sets the selected sampling frequency at different values during a single heart cycle.

15. A method for analyzing a cardiac activity in an implantable pacemaker device, comprising:
sensing the cardiac activity in the form of an analog signal,
obtaining sample data from the analog signal at a non-constant sample rate;
converting the analog signal into a representative digital signal using the sample data;
measuring a variation of the analog signal; and
setting the sample rate as a function of the variation measure, the sampling rate being increased as the variation of the analog signal increases and being decreased as the variation of the analog signal decreases.

16. The method of claim 15, wherein the sampling rate has an upper limit of approximately 800 Hz.

17. The method of claim 15, wherein the sampling rate has a lower limit of approximately 100 Hz.

18. The method of claim 15, wherein the sampling rate is decreased after a predetermined amount of time after the variation of the analog signal decreases.

19. The method of claim 18, wherein the predetermined amount of time is about 20 milliseconds.

20. The method of claim 15, wherein the sampling rate is increased variation measure comprises an analog signal amplitude change that exceeds a predetermined threshold corresponding to an analog signal frequency content greater than a predetermined cut-off frequency.

21. An implantable medical device system, comprising:
sampling means for sampling an analog signal at a sampling frequency to obtain digital representations of the analog signal, the analog signal being representative of intracardiac activity;
detector means for detecting the amplitude of the analog signal and generating first and second difference signals, the detector means generating the first difference signal after detection of a first amplitude change in the analog signal amplitude greater than a predetermined limit corresponding to an analog signal frequency content greater than a predetermined cut-off frequency, the detector means generating the second difference signal after detection of a second amplitude change in the analog signal amplitude less than the predetermined limit; and
frequency selector means for selecting the sampling frequency based on the first and second difference signal, the frequency selector means selecting a relatively higher sampling frequency in response to generation of the first difference signal and selecting a relatively lower sampling frequency in response to generation of the second difference signal.

* * * * *

UNITED STATES PATENT AND TRADEMARK OFFICE
CERTIFICATE OF CORRECTION

PATENT NO. : 7,292,168 B2
APPLICATION NO. : 11/320358
DATED : November 6, 2008
INVENTOR(S) : Willem Wesselink et al.

It is certified that error appears in the above-identified patent and that said Letters Patent is hereby corrected as shown below:

Col. 16, Line 18, delete "the sampling rate is increased variation" and insert in place there of --the variation--.

Signed and Sealed this

Sixth Day of January, 2009

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,292,168 B2 | |
| APPLICATION NO. | : 11/320358 | |
| DATED | : November 6, 2007 | |
| INVENTOR(S) | : Willem Wesselink et al. | |

It is certified that error appears in the above-identified patent and that said Letters Patent is hereby corrected as shown below:

Col. 16, Line 18, delete "the sampling rate is increased variation" and insert in place there of --the variation--.

This certificate supersedes the Certificate of Correction issued January 6, 2009.

Signed and Sealed this

Third Day of February, 2009

JOHN DOLL
*Acting Director of the United States Patent and Trademark Office*